United States Patent [19]

Ling et al.

[11] Patent Number: 5,171,275

[45] Date of Patent: Dec. 15, 1992

[54] FEMORAL STEM PROSTHESIS

[76] Inventors: Robin S. M. Ling, 2 The Quadrant, Wonford Rd., Exeter, England; W. E. Michael Mikhail, 4203 Shamley Green, Toledo, Ohio 43623; James J. Elting, 18 Brigham Rd., Oneonta, N.Y. 13820

[21] Appl. No.: 804,623

[22] Filed: Dec. 6, 1991

Related U.S. Application Data

[63] Continuation of Ser. No. 527,298, May 23, 1990, abandoned, which is a continuation-in-part of Ser. No. 480,229, Feb. 15, 1990, abandoned.

[51] Int. Cl.⁵ .......................... A61F 2/28; A61F 2/32
[52] U.S. Cl. ........................................ 623/16; 623/23
[58] Field of Search ..................... 623/16, 18, 20, 22, 623/23

[56] References Cited

U.S. PATENT DOCUMENTS

| | | | |
|---|---|---|---|
| Re. 32,488 | 9/1987 | Gustilo et al. | 623/18 |
| 3,793,650 | 2/1921 | Ling et al. | 625/18 |
| 3,829,904 | 8/1974 | Ling et al. | 623/18 |
| 3,965,490 | 6/1976 | Murray et al. | 623/23 |
| 3,986,212 | 10/1976 | Sauer | 623/18 |
| 4,279,042 | 7/1981 | Andriacchi et al. | 623/23 |
| 4,491,987 | 1/1985 | Park | 623/23 |
| 4,589,883 | 5/1986 | Kenna | 623/18 |
| 4,865,608 | 9/1989 | Brooker, Jr. | 623/23 |

FOREIGN PATENT DOCUMENTS 1409054  10/1975  United Kingdom ................ 623/23

OTHER PUBLICATIONS

SRN, "The SRN Total Hip Prosthesis" Brochure.
Article in *The Orthopedic Clinics of North America, Long-Term Results of Cemented Joint Replacement*, "Experience with Exeter Total Hip Replacement Since 1970", by J. L. Fowler MB, FRCS et al., dated Jul. 1988, published by W. B. Saunders Company, at pp. 477-489.
Article in *The Orthopedic Clinics of North America, Long-Term Results of Cemented Joint Replacement*, "Mechanical Failure in the Femoral Component in Total Hip Replacement", by Gordon Bannister, M. Ch. Orth, FRCS, at pp. 567-573 dated Jul. 1988, published by W. B. Saunders Company.
Booklet entitled "The Exeter Hip System-Seminar & Workshop" published by The University of Exeter, Exeter, England in 1983 by A. J. C. Lee and R. S. M. Ling.
Page 1 of Brochure entitled "The SRN Total Hip Prosthesis".
Pages 82-111 Proceedings of the Hip Society, 1980, Chapter 5, entitled "Total Hip Replacement Using a Collarless Femoral Prosthesis", by R. S. M. Ling.
Article entitled "Development of Cemented HIP-Stem Shapes for Optimal Load Transfer" by R. Huiskes and R. Boeklagen (date and publication unknown).

*Primary Examiner*—David Isabella
*Attorney, Agent, or Firm*—Emch, Schaffer, Schaub & Porcello Co.

[57] ABSTRACT

A tapered, collarless femoral hip joint prosthesis formed of Co-Cr-Mo alloy with highly polished surfaces is provided.

20 Claims, 6 Drawing Sheets

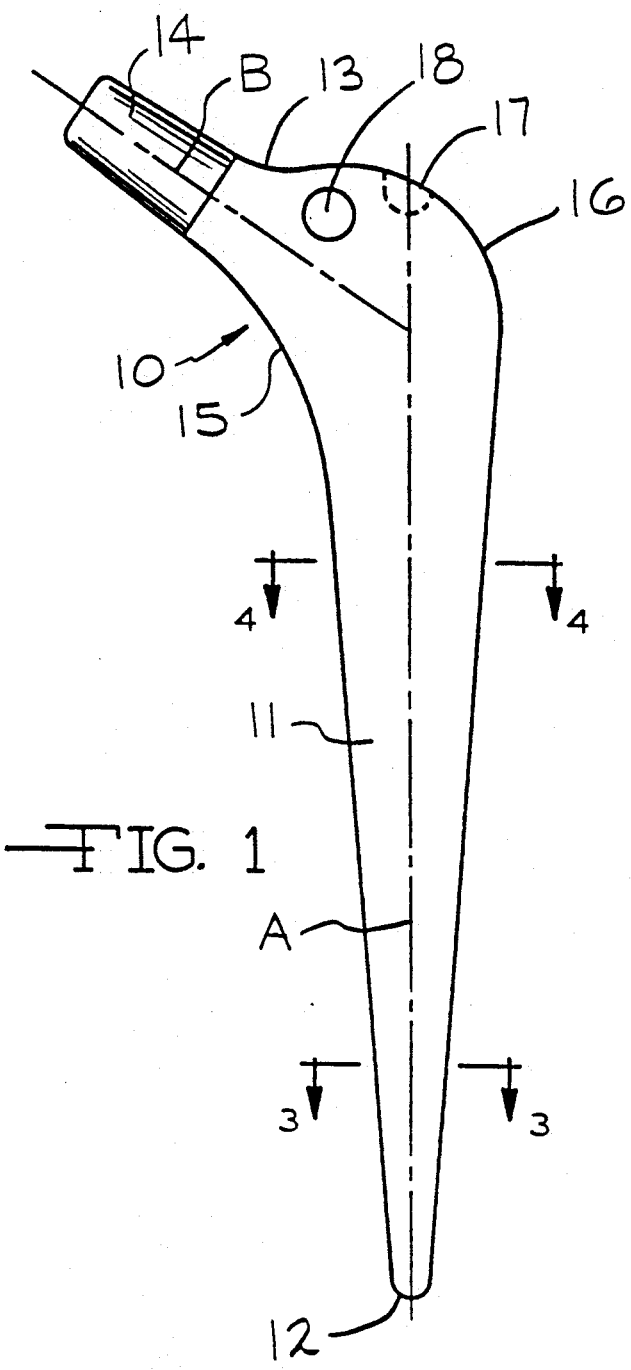
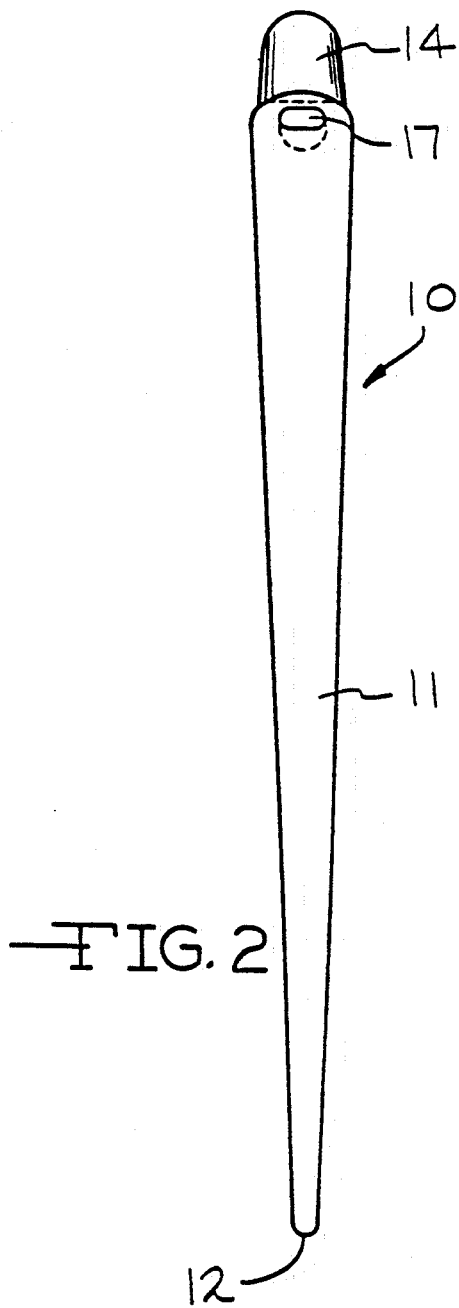
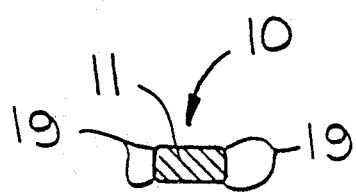
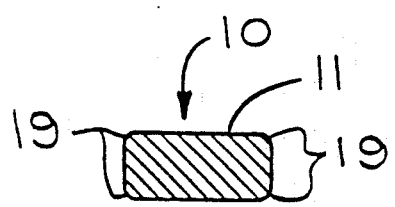

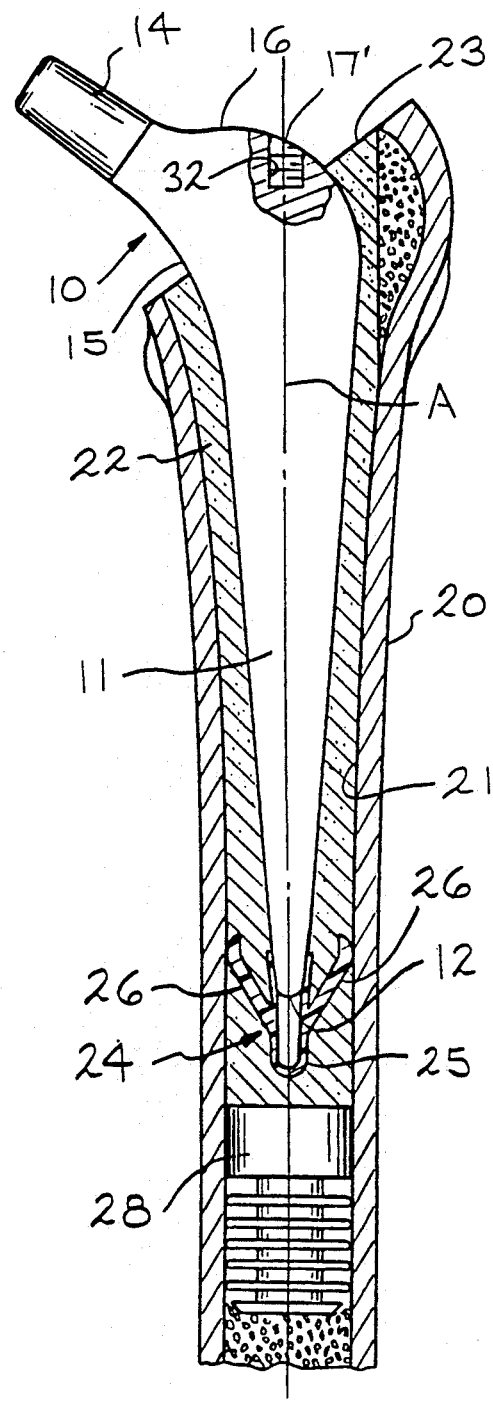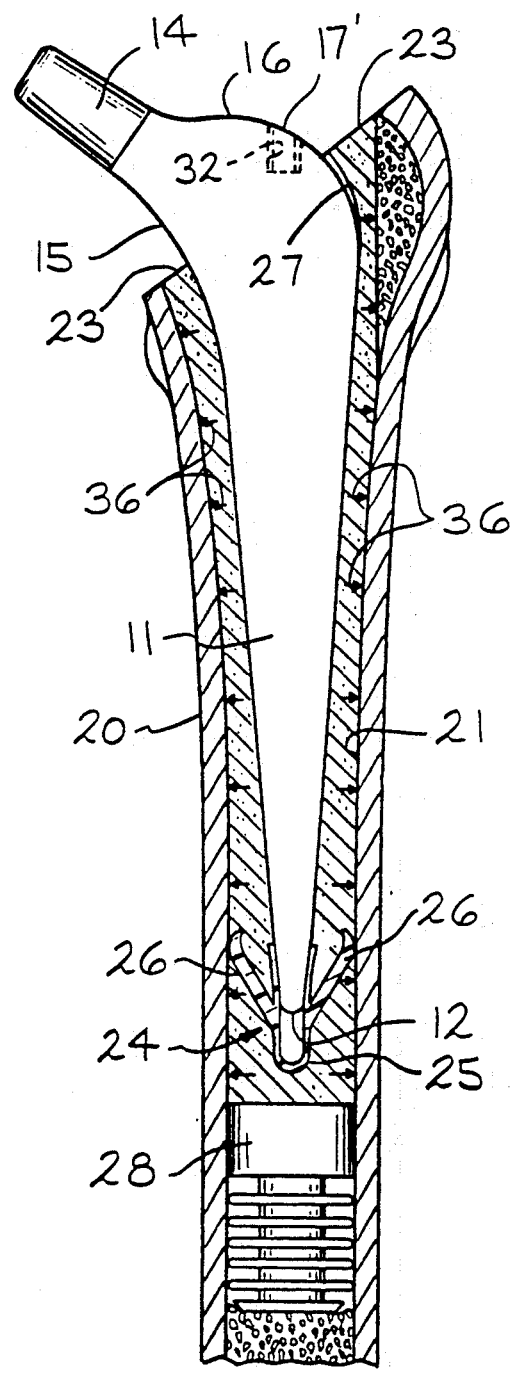

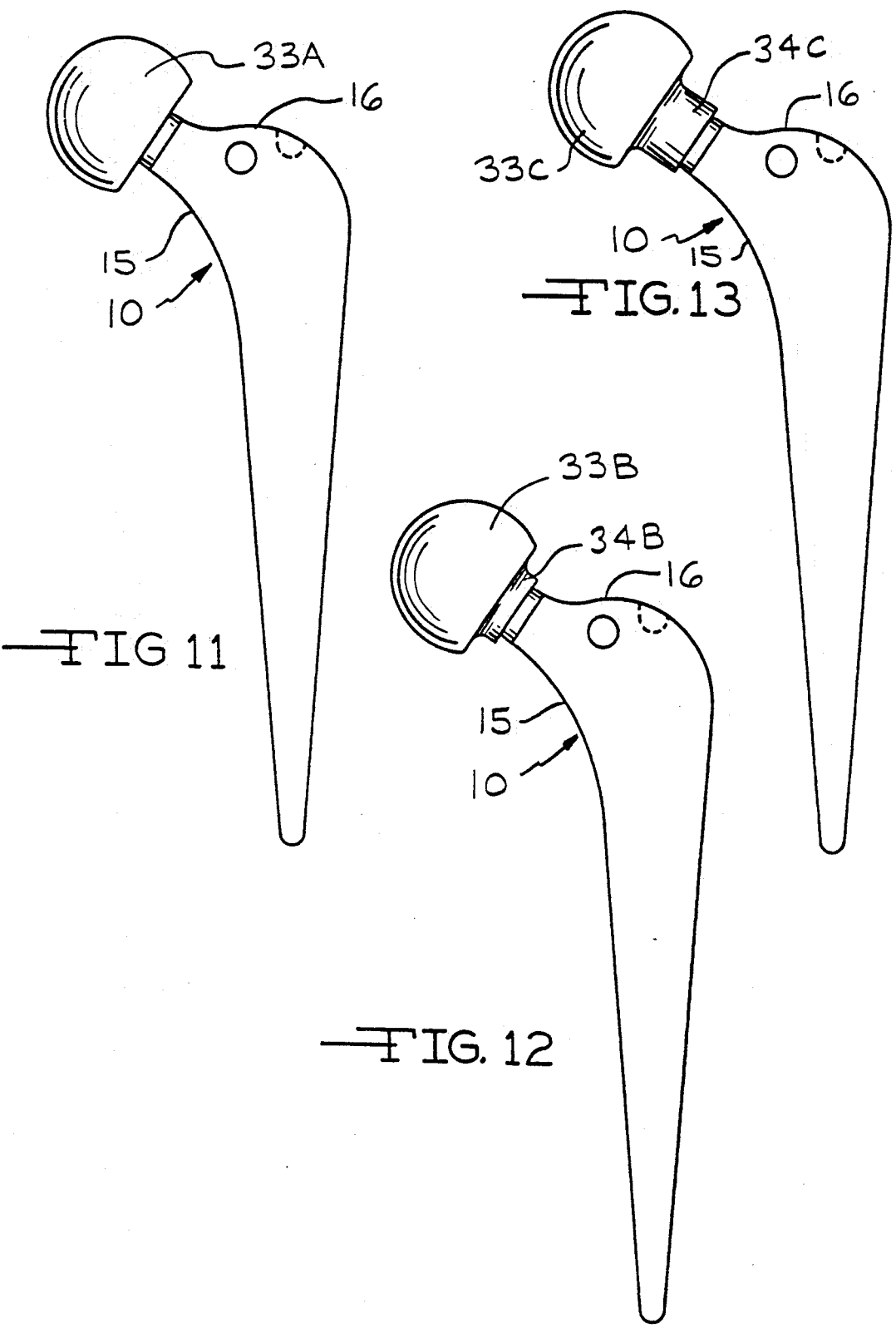

FEMORAL STEM PROSTHESIS

CROSS REFERENCE TO RELATED APPLICATION

This is a continuation of copending application Ser. No. 07/527,298 filed on May 23, 1990, now abandoned, which is a continuation-in-part of application Ser. No. 07/480,229, filed Feb. 15, 1990, now abandoned.

BACKGROUND OF THE INVENTION

The present invention relates to a hip joint prosthesis and more particularly to the femoral component of such a prosthesis.

Many methods and devices have been developed to improve the fixation of hip joint prostheses including the femoral component thereof in the body so that the device implanted therein becomes as permanent as possible. Many orthopedic implants use a cement to anchor the stem portion of a femoral component in the femur. For example, United Kingdom Patent Specification No. 1,409,054 in the names of Robin S. M. Ling (one of the co-inventors of the present appliation) and Alan J. C. Lee (incorporated herein by reference) discloses a hip joint prosthesis having a double-tapered stem which, among other advantages, enhances extrusion of cement caused by penetration of the stem during fixation. U.S. Pat. No. 3,793,650, (incorporated herein by reference) one of the co-inventors of which is also Robin S. M. Ling, discloses an intramendullary stem for a prosthetic bone joint device having a base with spring members intended to centralize the position of the stem in the canal or bore of the bone in order to insure a relatively uniform or, at least minimum thickness of cement between the wall of the bone and the stem. It is desirable that there be at least two millimeters (2 mm) of cement between the stem and the bone. By providing a means for insuring that there will be at least a certain minimum thickness of cement between the stem of the prosthesis and the interior wall of the canal formed in the femur bone for receiving such stem, the likelihood of the stem protruding through the cement and contacting the interior of the femur bone itself is minimized. Thus, in those types of implants using cement, it is important to insure that the stem is completely encapsulated by the cement and does not protrude through to contact the bone.

One type of bone cement utilized to retain the stem of a femoral hip joint prosthesis in the canal of a bone comprises a mixture of polymethylmethacrylate (hereinafter PMMA) polymer and methyl methacrylate monomer and optionally including a styrene co-polymer of PMMA. This and other types of cement utilized for such purpose may be packaged in two separate components which are mixed into a paste which is placed in the canal of the femur immediately prior to insertion of the stem of the prosthesis. Such paste then sets to a relatively rigid material providing excellent adherence to the interior wall of the bone.

Heretofore, it has been the belief that it is desirable to have good adhesion between the stem and the cement. Many prior art devices were specifically directed to providing a design for the prosthesis intended to maximize adhesion between it and the cement. For example, the CML Cemented Medullary Locking Hip System manufactured by DePuy Division of Boehringer Mannheim Corporation, Warsaw, Ind., is a hip system in which the upper portion of the stem is provided with a roughened textured surface intended to enhance the bond of the cement to the prosthesis at the prosthetic interface. It also utilizes a "Macro-Textured" waffle design which is intended to increase the surface area and the mechanical interlock between the cement and the prothesis in the area of such waffle design.

Osteonics Corp., Allendale, N.J., manufactures the OMNIFLEX Femoral System of a titanium alloy having a normalized surface to promote good adhesion of the cement thereto.

U.S. Pat. No. 4,281,420 (incorporated herein by reference) is directed to maximizing the strength and durability of the prosthesis/cement adherence.

Other types of devices which disclose the use of cement within a bore or canal of the femur are described in U.S. Pat. Nos. 3,829,904; 3,874,003; 4,012,796; and 4,080,666, the disclosures of which are hereby incorporated by reference. Copies of such patents are enclosed.

Still other types of prostheses are intended for use without cement. Many of these are designed to provide a porous or roughened surface in order that the bone may grow into the porous surface of the prosthesis. For example, U.S. Pat. No. 3,808,606 discloses a prosthesis possessing porous surfaces for fixation by tissue ingrowth. U.S. Pat. No. 4,164,794 discloses prosthetic devices having outer foamed or sintered porous coatings of selected bioengineered thermoplastics which enables the device to become firmly anchored to the bone by tissue ingrowth into the coated material.

In both the cemented and non-cemented types of devices used heretofore, problems have arisen, particularly after a number of years of implantation. With respect to the cemented type devices, part of the problem arises from the fact that the cement utilized to retain the stem of the device in the canal of the femur bone is subject to a phenomenon known as creep. Thus, while the bone cement appears to be rigid when set, it is subject to minute amounts of movement over time. The amount of creep encountered with such cement following implantation is exaggerated by virtue of the fact that the body temperature controls the temperature of the implanted cement and prosthesis. Thus, PMMA and other types of bone cement at body temperature are subject to a greater degree of creep than bone cement maintained at room temperature of, say, 72° F. This may be readily observed by mounting a bar of PMMA so that its ends are supported and applying a fixed load at the center of the bar. Tests have shown that a bar so supported and subjected to a load of 5 pounds for eight hours at 98.6° F. will deflect to an extent 3.5 times greater than an identical bar supported and loaded in an identical manner for eight hours at 72° F.

Over a period of time, the phenomenon of creep may result in disruption of the micro-interlocking of the cement-bone interface, especially if the cement mantle is firmly bonded to the femoral prosthesis. As is well known in the field of hip replacements, it is important that there be a good bond between the cement and the bone and that there be no disruption in the micro-interlocking of the cement-bone interface.

Subsidence of the femoral component occurs in various degrees with prostheses of different designs regardless of the presence or absence of collars. Any firmly bonded or fixed prosthesis to the cement will disrupt the cement bone interface which will inevitably lead to clinical loosening and subsequent failure necessitating revision.

SUMMARY OF THE INVENTION

The present invention provides for a femoral hip joint prosthesis having a design which allows for subsidence of the stem within the cement mantle without disrupting the micro-interlocking in the cement-bone interface.

Accordingly, it is an object of the present invention to provide a new and novel femoral hip joint prosthesis which is specifically designed to avoid the forementioned problems resulting from subsidence of the stem and physical properties of the cement at different temperatures.

It is a further object of the present invention to provide a femoral hip joint prosthesis which will not loosen but rather will self-tighten even though the cement mantle creeps or expands fractionally over a period of time.

It is yet another object of the present invention to provide a femoral hip joint prosthesis in which the stem subsides within the cement as the cement creeps and, thus, is permitted to remain at all times in snug interfacial contact therewith, imparting in the stem area the reliable compressive forces against the cement which is micro-interlocked with the bony surfaces.

It is another object of the present invention to provide a femoral hip joint prosthesis which self compensates and subsides within a cement mantle as such cement mantle creeps over time without disrupting the micro-interlocking and thus preserving the cement-bone interface.

The femoral hip joint prosthesis of the present invention is collarless, has a double tapered stem formed of cobalt chrome molybdenum alloy and has the surface of the stem highly polished to provide an extremely smooth surface which should not exceed maximum level of roughness. The lower end of the stem is positioned in a hollow centralizer which serves to stabilize it and insure that an adequate thickness of cement encapsulates the stem. Such design permits the stem portion of the prosthesis to move fractionally within the cement mantle without disrupting the cement-bone interface and to self-tighten as the male component, namely, the distal tip of the stem engages further in the hollow centralizer.

Although prior art prostheses such as the tapered collarless bone joint devices disclosed in the previously referenced United Kingdom Patent Specification No. 1,409,054 and U.S. Pat. No. 3,793,650 have been used with polished surfaces, they have never utilized chrome cobalt alloy with the roughness tolerance as set forth in the present invention. The prosthesis of the present invention provides superior results over the prior art in that, as well as allowing subsidence within the cement mantle, it exhibits good corrosion resistance when implanted in the body. The absence of a collar is important to provide a prosthesis in which there is no mechanical interference with any such subsidence. The combination of medial cement buttress and absence of a collar prevent the stem from going into varus when subsidence occurs.

Additionally, the femoral hip joint prosthesis of the present invention at the proximal end opposite the stem is contoured to provide a smooth transation to a Morse taper which may receive Morse Taper Heads of varying neck lengths and diameters (i.e. 22, 26, 28, 32 mm).

Finally, it is an object of the present invention to provide a femoral hip joint prosthesis in combination with a cement mantle implanted in the canal of a femur wherein said cement mantle encapsulates the stem of such prosthesis in an interfacial relationship which permits subsidence of the stem within the cement mantle without disrupting the interfacial adherance between the cement mantle and the bone.

BRIEF DESCRIPTION OF THE DRAWINGS

FIG. 1 is a front elevational view of the femoral hip joint prosthesis, according to the present invention;

FIG. 2 is an end view of such femoral hip joint prosthesis;

FIG. 3 is a sectional view taken through line 3—3 of FIG. 1;

FIG. 4 is a sectional view taken through line 4—4 of FIG. 1;

FIG. 7 is a sectional view showing the femoral hip joint prosthesis of the present invention immediately after implanting in a patient;

FIG. 8 is a view similar to FIG. 7 showing the femoral hip joint prosthesis after being implanted for a number of years and showing, greatly exaggerated, the effects of subsidence;

FIGS. 11-13 are elevational views showing the femoral hip joint prosthesis of FIG. 1 in combination with Morse Taper Heads of various lengths.

DETAILED DESCRIPTION OF THE DRAWINGS

Figure 5:
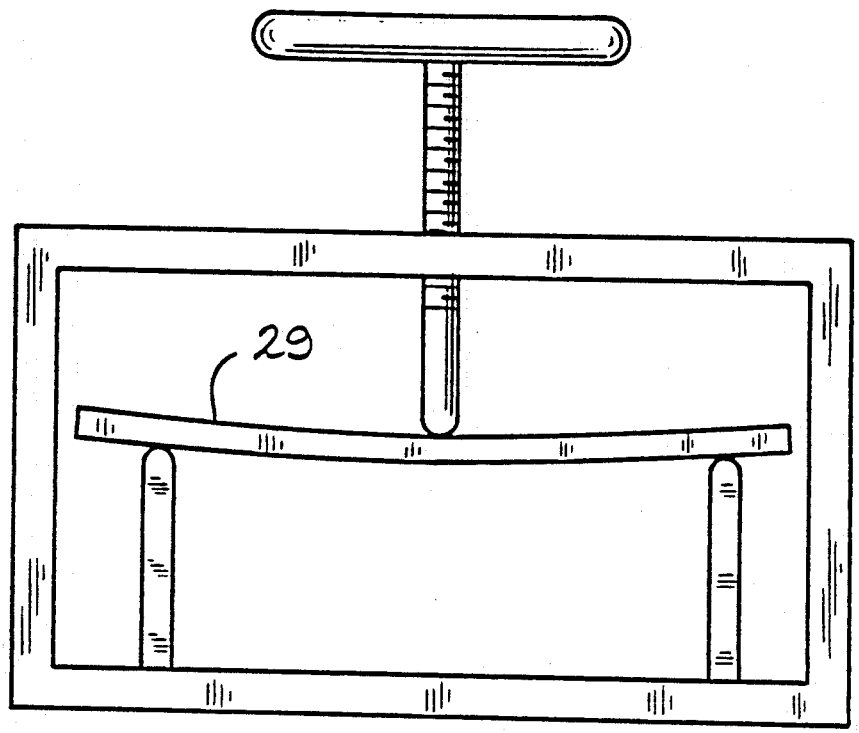
FIGS. 5 and 6 are schematic views showing the difference in the amount of deflection occurring in a test bar of PMMA bone cement supported at its ends and subjected to a constant load of 5 pounds for eight hours at room temperature (FIG. 5) and at a temperature approximating body temperature (FIG. 6)

Referring now to FIGS. 1 and 2, there is shown a femoral hip joint prosthesis 10 having a stem 11 which is convergently tapered toward a distal end 12 and extending along a first axis of symmetry A to an area of juncture with a neck portion 13 lying on a second axis of symmetry B. Extending from the neck portion 13 is a frustoconically shaped Morse Taper Neck 14 to which may be attached a spherically shaped Morse Taper Head. As is clear from FIG. 1, no collar is provided in the femoral hip prosthesis, but rather the portion of the prosthesis joining the stem 11 to the neck 13 follows a smooth arcuate contour in the area 15 of the included angle between the respective axes of symmetry A and B. The portion of the femoral hip prosthesis 10 opposite the smooth arcuate portion 15, namely, that portion on the outside of the angle between the two axes of symmetry A and B, has an enlarged shoulder 16 in which is formed a dimple or recess 17 for driving the prosthesis into the femur. As can be seen, the dimple 17 is located on the first axis of symmetry A.

An aperture 18 is provided in the area of the neck and shoulder to assist in removing the prosthesis 10 in the event revision is required at some future time.

As can be seen in FIGS. 3 and 4, the stem 11 is tapered in both directions and has rounded corners 19. As pointed out in United Kingdom Patent Specification 1,409,054, such double tapering enhances the extrusion of cement caused by penetration of the stem 11 thereinto during fixation.

The femoral hip joint prosthesis 10 of the present invention is formed of high-strength forged Co-Cr-Mo alloy (ASTM designation F-799) and has its surface polished to a high degree (also known as a color buff finish) to provide for a smoothness having a target surface roughness of four (4) microinches. It has greater fatigue strength, corrosion resistance and wear resistance than stainless steel. Additionally, it resists pitting and crevice corrosion in the body environment.

It is the combination of the Co-Cr-Mo alloy having its surface polished to the above target coupled with the tapered stem and collarless design which permits the femoral hip prosthesis of the present invention to function in the manner intended without loosening and without causing pain or other adverse mechanical effects in the patient even though there is subsidence of the prosthesis over a period of time. Thus, the present design permits the polished stem to subside within the cement mantle. The taper of the stem permits it to self-tighten upon the slight movement which occurs during the subsidence and engage in the hollow centralizer and yet to do so without pulling the cement mantle and thus avoid disrupting the micro-interlocking at the cement-bone interface. Such design causes the stem to impart primarily compressive forces against the cement mantle, thus transmitting the load to the femur. Transmitting the load in this manner forces the cement mantle continuously snugly and firmly against the interior of the femur to assist in maintaining the integrity of the micro-interlocking at the cement-bone interface.

Referring now to FIG. 5, a bar 29 of PMMA cement 80 mm inches long and having a rectangular cross section of 10 mm by 3 mm inches was supported on point supports 75 mm apart and subjected to a load at its midpoint of 3.9 kg. while being maintained at a temperature of 72° F. for ten hours. Such loading resulted in a deflection of 4.3 mm.

Figure 6:
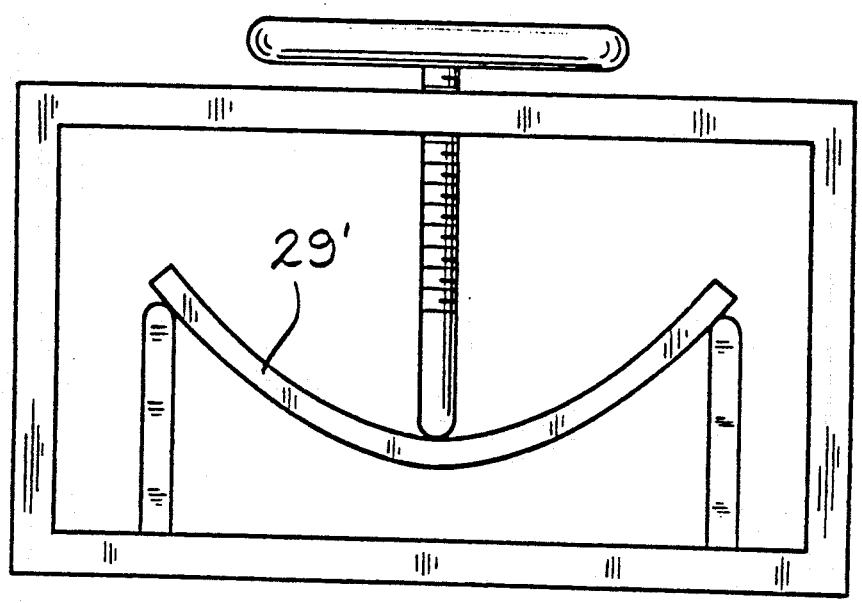

FIG. 6 illustrates an identical bar 29' loaded in the same manner except at a temperature of 98.6° F. The bar 29' had a deflection of 15 mm inches at the end of such ten hour period.

Referring now to FIG. 7, there is shown the femoral hip joint prosthesis 10 of the present invention immediately following its implantation in the femur bone 20. As is customary, the femur bone 20 is prepared by reaming a canal 21 into which PMMA or other suitable bone cement is introduced under pressure. Promptly after introduction of the bone cement into the canal 21 and before the cement has had an opportunity to set, the stem 11 of the femoral hip joint prosthesis 10 is inserted into the cement with the result that a cement mantle 22 is formed around the stem 11 up to the arcuate area 15 and a portion of the enlarged shoulder 16. Any excess cement is wiped away leaving an exposed upper end 23.

The free or distal end 12 of the stem 11 is engaged in a hollow plastic centralizer 24 which insures that there will be a sufficient thickness of cement around all portions of the stem. The plastic centralizer 24 includes a cup-shaped pocket 25 having a plurality, preferably 3 or 4, of integrally formed resilient arms 26 sized to engage the interior of the canal 21. The hollow cup-shaped pocket 25 of the centralizer may be filled with a compressible material such as Avitin Powder, Surgicell, Gelfoam or the like such that there will be no interference with subsidence of the distal end 12 of the prosthesis 10 within the hollow pocket 25 of the centralizer. Prior to introduction of cement in the canal, a cement restrictor 28 is positioned therein.

FIG. 8 shows the implanted femoral hip joint prosthesis 10 after an extended period, say ten years, following implantation. As can be seen there has occurred a small amount of radiological subsidence, on the average of 2 mm, where the stem 11 has subsided within the cement mantle 22. As may be seen in FIG. 8, such subsidence within the cement mantle results in the distal end 12 moving further into the centralizer 24 and in the enlarged shoulder 16 pulling away from the cement mantle 22 leaving a gap 27. Because of the tapered-stem, collarless design of Co-Cr-Mo alloy having a highly polished surface, the femoral hip joint prosthesis 10 of the present invention is permitted to subside within the cement mantle 22 but to do without disrupting the cement-bone interface. Thus, the subsidence of the stem 11 results in microscopic movement of the stem 11 in relation to the adjacent surface of the cement mantle 22. As will be appreciated and as shown schematically in FIG. 8, the effect of such microscopic movement is to cause the stem 11 to self-tighten as it and the cement mantle 22 subside and to impart primarily compressive forces against the cement mantle 22 in directions substantially normal to the interior surfaces of the bone 20. This is illustrated schematically by the arrows 36 in FIG. 8.

The hip joint prosthesis 10 shown in FIGS. 7 and 8 incorporates a modification in that the dimple 17' is drilled to a deeper depth than the dimple 17 of FIGS. 1 and 2 and is tapped to form internal threads 32. The threaded dimple 17' may then serve the dual function of assisting with insertion of the hip joint prosthesis 10 and, in the event replacement is required, with its removal. As can be seen from FIGS. 7 and 8, with this modification, no hole is provided in the shoulder 16. As will be appreciated, a tool (not shown) engages the threads 32 to assist in such insertion or removal.

Figure 9:
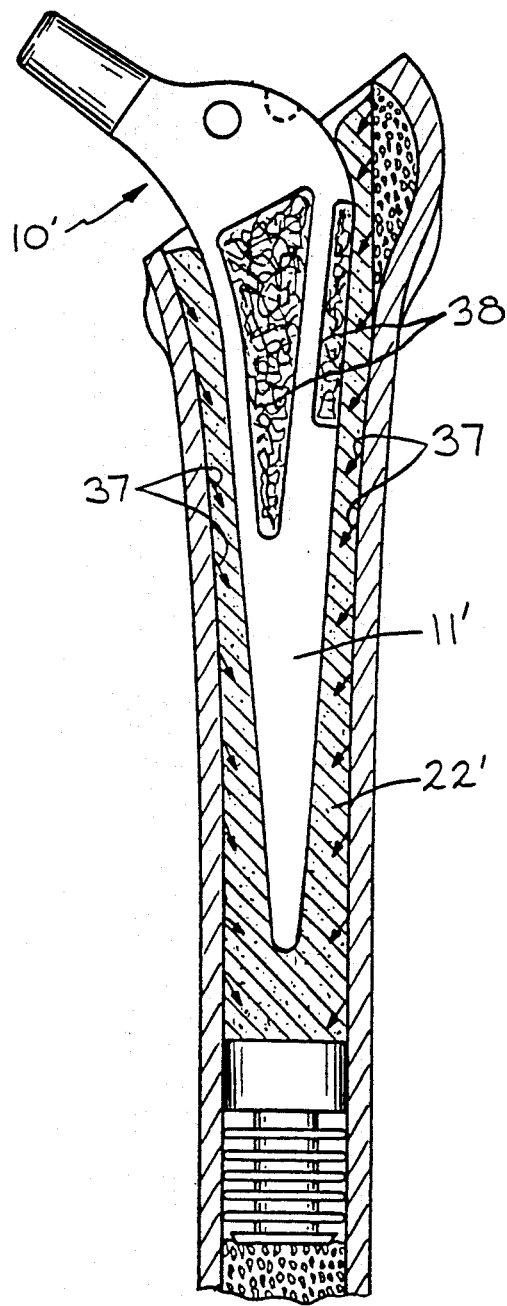
FIG. 9 is a view similar to FIG. 8 showing the difference in the effect of the subsidence on a femoral hip joint prosthesis of the type in which the cement is rigidly adhered to the femoral hip joint prosthesis.

FIG. 9 shows schematically the effect of subsidence of the bone cement 22' on a femoral hip joint prosthesis 10' having a similar configuration as that of femoral hip joint prosthesis 10 of the present invention but having a porous or other type surface 38 to which the bone cement may become firmly bonded to create an interlocked stem-cement mantle interface. As can be seen from the schematic, the subsidence of the stem 11' to which the cement mantle 22' is firmly bonded, will cause the cement mantle 22' to be pulled downwardly with the stem 11' as it subsides thus placing tension upon the interface between the cement mantle 22' and the bone, causing an undesirable disruption in the microinterlocking of the bone-cement interface and inevitable subsequent loosening thereof. Such tension on the interface between the cement mantle 22' and the bone 20 is illustrated schematically by the arrows 37 as the stem 11' tends to pull with it the adjacent portions of the cement mantle 22' bonded thereto.

Figure 10:
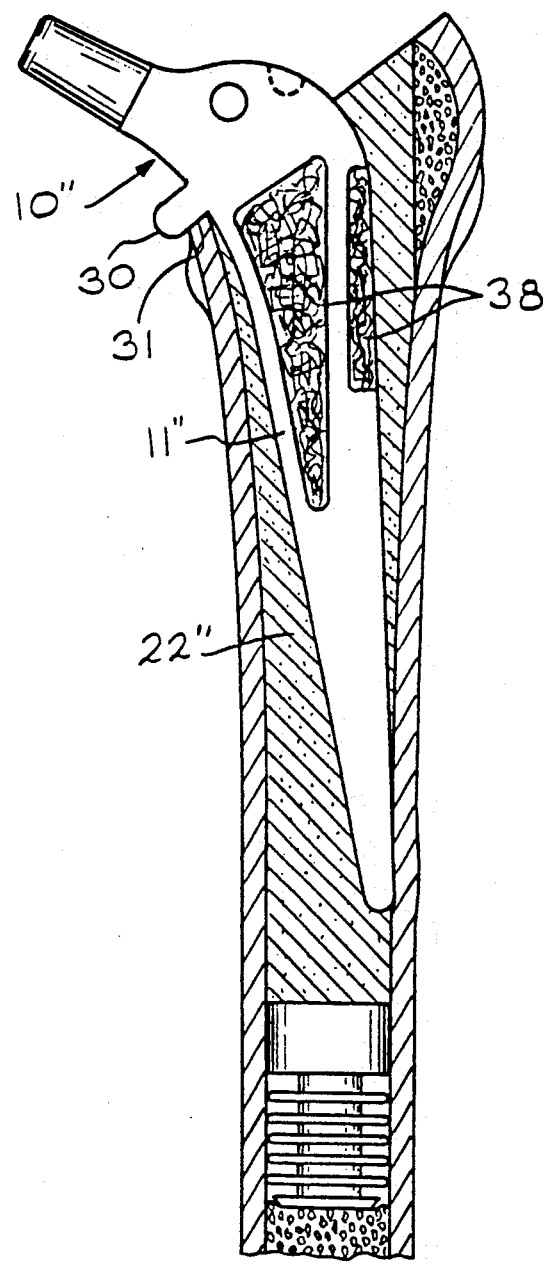
FIG. 10 is a view of a femoral hip joint prosthesis having a collar after being implanted for a number of years and showing the effect of subsidence on a prosthesis having a collar.

FIG. 10 shows the undesirable effect of subsidence on a femoral hip joint prosthesis 10" having a collar 30. In those types of prostheses having collars such as that illustrated by the collar 30 in FIG. 10, the prosthesis is positioned during implantation with the collar 30 resting upon the top 31 of the prepared femur. As can be seen in FIG. 10, such collar 30 interferes with subsidence of the stem 11" within the cement mantle 22" with the result that the stem 11" becomes cocked in the canal of the femur and may, in extreme cases, be forced through the cement mantle and into contact with the interior of the bone causing great discomfort to the patient. Additionally, the pressure of such collar 30 against the top 31 or calcar of the prepared femur, causes a substantial wearing away of the calcar.

Referring now to FIGS. 11–13, there is shown three different Morse Taper Heads 33A (FIG. 11), 33B (FIG. 12) and 33C (FIG. 13). As can be seen from a comparison, Morse Taper Head 33A has no neck, Morse Taper Head 33B has a short neck 34B and Morse Taper Head 33C has a relatively long neck 34C. This permits effective elongation of the stem into the canal. The surgeon will make a determination during implantation of which of the Morse Taper Heads to use with a given patient based upon a number of factors based upon the leg length and stability of the prosthesis. Additionally, the heads 33A, 33B and 33C may be provided with different diameters ranging from 22, 26, 28 to 32 mm.

As can be seen from the drawings, the prosthesis 10 follows a smooth contour from the arcuate area 15 on one side and the enlarged shoulder 16 on the other side to the frustoconically shaped portion forming the Morse Tapered Neck 14. The absence of any protrusions in such area is a factor which permits the effective subsidence of the prosthesis 10 of the present invention within the cement mantle.

Referring now to FIGS. 14–18, there is provided a modified femoral hip prosthesis 50 having a stem 51 which is convergently tapered toward the distal end 52 and extending along a first axis of symmetry C to an area of juncture with an neck portion 53 lying on a second axis of symmetry D. Extending from the neck portion 53 is a frustoconically-shaped Morse Taper Neck 54 to which may be attached a spherically-shaped Morse Taper Head. As in the previous embodiments, no collar is provided in the femoral hip prosthesis 50, but rather the portion of the prosthesis joining the stem 51 to the neck 53 follows a smooth arcuate contour in the area 55 of the included angle between the respective axes of symmetry C and D. The portion of the femoral hip prosthesis 50 opposite the smooth arcuate portion 55, namely, that portion on the outside of the angle between the two axes of symmetry C and D has an enlarged shoulder 56. As may be seen in FIG. 14, in profile the shoulder 56 includes a lower portion 57 which follows a straight line path aligned with the straight line path followed by a stem 51 and an upper portion 58 which follows a smooth slightly curved path merging with the neck portion 53.

Figure 15:
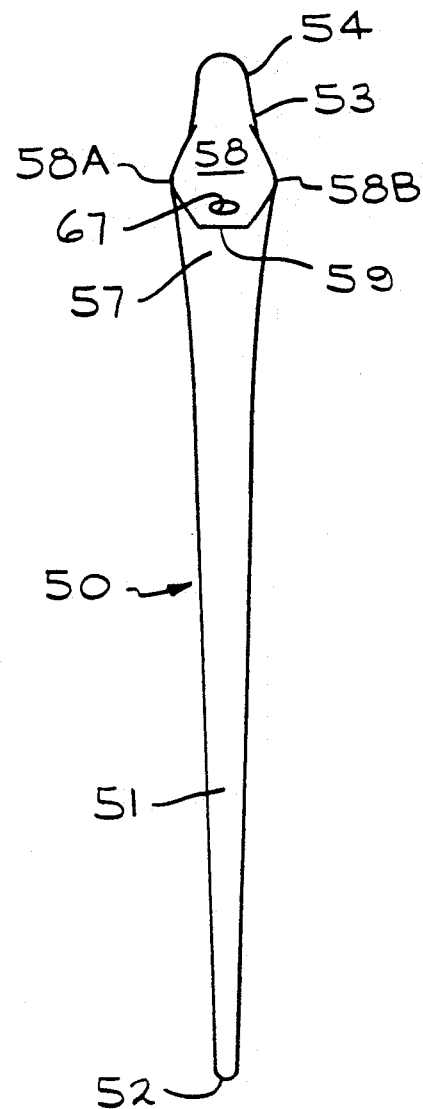
FIG. 15 is an end view of the femoral hip joint prosthesis of FIG. 14.

As may be seen from FIG. 15, the upper portion of the shoulder 58 follows a straight line path from one edge 58A to the opposite edge 58B. The area of juncture between the lower portion 57 and upper portion 58 provides a sharp line of demarcation 59 at the outer most portion of the shoulder 56.

Figure 14:
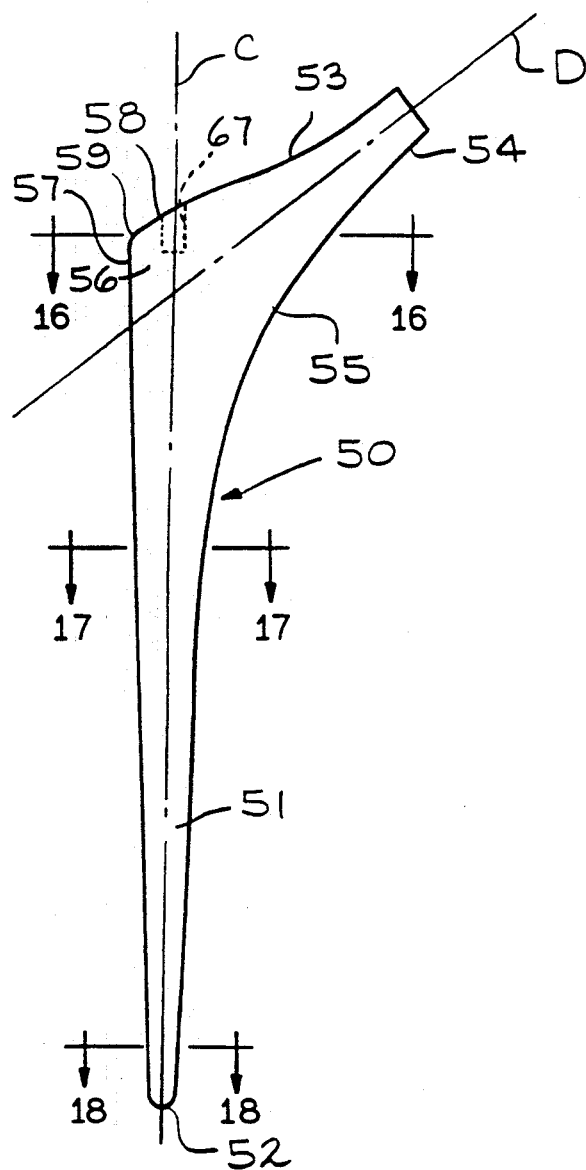
FIG. 14 is a front elevational view of another embodiment of the femoral hip joint prosthesis according to the present invention.

As may be seen in FIG. 14, the stem 51 diverges away from the axis C as it extends from the distal end 52 toward the shoulder 56. As may be seen from FIGS. 18 and 17, the stem 51 has a circular cross-sectional configuration near the distal end 52 and an oval configuration in the area approaching the arcuate area 55 and the shoulder 56 with the areas therebetween merging between circular and oval.

Figure 16:
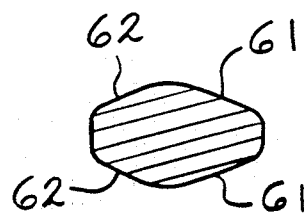
FIG. 16 is a sectional view taken through line 16—16 of FIG. 14.
Figure 17:
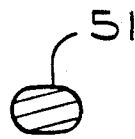
FIG. 17 is a sectional view taken through line 17—17 of FIG. 14.
Figure 18:
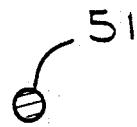
FIG. 18 is a sectional view taken through line 18—18 of FIG. 14.

Additionally, as may be seen in FIG. 16, the cross-sectional configuration in the area through the neck 53 and upper portion 58 of the shoulder 56 has a generally oval configuration with flattened segments 61 and 62 on opposite sides. Other cross-sectional configurations may be utilized in this area provided it merges smoothly with the stem 51 and the neck 53.

As in the previous embodiment, the upper portion 58 of the shoulder 56 may have formed therein a dimple or recess 67 which may, if desired, have internal threads (not shown). As in the previous embodiment, the dimple 67 is located on the first axis of symmetry C.

The present invention of a femoral hip joint prosthesis, formed of Co-Cr-Mo alloy with a highly polished surface, collarless and a tapered stem, permits patients to enjoy long lasting and predictable results.

Modifications will be readily apparent to those skilled in the art. Accordingly, the present invention should be limited only by the scope of the claims.

We claim:

1. A method for implanting a femoral hip joint prosthesis in a prepared intramedullary canal comprising the step of:
    (a) providing a prosthesis having an elongated stem extending from a proximal end to a distal end and defining a first axis, said proximal end having a neck region which joins the stem at a juncture, said stem having anterior, posterior, medial and lateral surfaces and said surfaces tapering downwardly from said juncture to said distal end; said neck region defining a second axis disposed at an obtuse angle with the first axis, and said medial surface defining a smooth arcuate path from the stem across the juncture to the neck region and said lateral surface defining an enlarged shoulder proximal said juncture; and said stem being formed of a cobalt chrome molybdenum alloy and said surfaces having a polished finish throughout such that substantially no interfacial bonding will occur between such surfaces and bone cement in contact therewith;
    (b) placing cement in said intramedullary canal;
    (c) inserting said prosthesis, distal end first into said intramedullary canal such that substantially all of said stem is encapsulated within said cement;
    (d) permitting said cement to set forming an interfacial bond with bone surface of said intramedullary canal and a support for said stem; and
    (e) thereafter permitting said stem to subside within said cement without disrupting said interfacial bond.

2. The method according to claim 1, wherein said polished finish is provided with a surface roughness no greater than 4 microinches to provide enhanced subsidence of said stem within said cement without disrupting said interfacial bond.

3. The method according to claim 1, wherein said stem is provided with a rectangular configuration with rounded corners.

4. The method according to claim 1, wherein said stem is provided with a cross-sectional configuration which is circular in an area adjacent said end, oval in the area between said distal end and said enlarged shoulder and merges between circular and oval in the area therebetween.

5. The method according to claim 1, wherein said enlarged shoulder is provided with an arcuate path from said neck to said stem.

6. The method according to claim 1, wherein said enlarged shoulder is provided with a lower portion which follows a straight line path aligned with the portion of said stem on the outside of said obtuse angle and an upper portion following a smooth path to said neck.

7. A method for implanting a femoral hip joint prosthesis in a prepared intramedullary canal comprising the steps of:
   (a) providing a prosthesis having an elongated stem extending from a proximal end to a distal end and defining a first axis, said proximal end having a neck region which joins the stem at a juncture, said stem having anterior, posterior, medial and lateral surfaces and said surfaces tapering downwardly from said juncture to said distal end; said neck region defining a second axis disposed at an obtuse angle with the first axis, and said medial surface defining a smooth arcuate path from the stem across the juncture to the neck region and said lateral surface defining an enlarged shoulder proximal said juncture; and said stem being formed of a cobalt chrome molybdenum alloy and said surfaces having a polished finish throughout such that substantially no interfacial bonding will occur between such surfaces and bone cement in contact therewith;
   (b) placing in said intramedullary canal
      (i) a centralizer having an open upper end sized to receive said distal end and
      (ii) cement
   (c) inserting said prosthesis, distal end first into said intramedullary canal such that substantially all of said stem is encapsulated within said cement and said distal end is engaged in the open upper end of said centralizer;
   (d) permitting said cement to set forming an interfacial bond with bone surface of said intramedullary canal and a support for said stem; and
   (e) thereafter permitting said stem to subside within said centralizer and within said cement without disrupting said interfacial bond.

8. The method according to claim 7, wherein said polished finish is provided with a surface roughness no greater than 4 microinches to provide enhanced subsidence of said stem within said cement without disrupting said interfacial bond.

9. The method according to claim 7, wherein said stem is provided with a rectangular configuration with rounded corners.

10. The method according to claim 7, wherein said stem is provided with a cross-sectional configuration which is circular in an area adjacent said end, oval in the area between said distal end and said enlarged shoulder and merges between circular and oval in the area therebetween.

11. The method according to claim 7, wherein said enlarged shoulder is provided with an arcuate path from said neck to said stem.

12. The method according to claim 7, wherein said enlarged shoulder is provided with a lower portion which follows a straight line path aligned with the portion of said stem on the outside of said obtuse angle and an upper portion following a smooth path to said neck.

13. A method for implanting a femoral hip joint prosthesis in an intramedullary canal comprising the steps of:
   (a) providing a prosthesis having an elongated stem extending from a proximal end to a distal end, said stem tapering from a relatively larger cross-sectional size adjacent said proximal end to a smaller cross-sectional size adjacent said distal end and being formed of a cobalt chrome molybdenum alloy and having substantially all surfaces with a polished finish having a surface roughness no greater than 4 microinches;
   (b) placing cement in said intramedullary canal;
   (c) inserting said prosthesis, distal end first, into said intramedullary canal such that substantially all of said stem is encapsulated within said cement;
   (d) permitting said cement to set forming an interfacial bond with bone surface of said intramedullary canal and a support for said stem; and
   (e) thereafter permitting said stem to subside within said cement without disrupting said interfacial bond.

14. The method according to claim 13, wherein said stem is provided with a cross-sectional configuration which is rectangular with rounded corners.

15. The method according to claim 13, wherein said stem is provided with a cross-sectional configuration which is circular in an area adjacent said distal end, oval in the area between said distal end and said proximal end and merges between circular and oval in the area therebetween.

16. The method according to claim 13 further including the steps of:
   (i) placing a centralizer having an open upper end in said intramedullary canal prior to the step of inserting said prosthesis and said distal end is positioned within said centralizer open upper end upon completion of said step of inserting, and
   (ii) permitting said distal end to move further into said centralizer upon said step of permitting said stem to subside within said cement.

17. The method according to claim 7, wherein said centralizer has a closed lower end and an annular wall extending between said open upper end and said closed lower end defining a pocket and wherein said distal end is spaced from said closed lower end both before and after step (e).

18. The method according to claim 17 further including the step of placing compressible material in said pocket prior to the step of said distal end becoming engaged with said centralizer.

19. The method according to claim 13 further including the steps of:
   (i) engaging to said distal end a centralizer having an annular wall with an open upper end and a closed lower end defining a pocket, the size of said open upper end and distance to said closed lower end in relation to the size and degree of taper of said stem at said distal end being such that said distal end is spaced from said closed lower end, and
   (ii) permitting said distal end to move further into said centralizer pocket upon said step of permitting said stem to subside within said cement.

20. The method according to claim 19 further including the step of placing compressible material in said pocket prior to the step of engaging said distal end and said centralizer.

* * * * *